(12) United States Patent
Chaubron et al.

(10) Patent No.: US 6,309,838 B1
(45) Date of Patent: Oct. 30, 2001

(54) METHOD FOR DETECTING QUALITATIVE AND QUANTITATIVE ALTERATIONS IN DNA AND LIGANDS OF SAID ALTERATION LIGANDS

(75) Inventors: Franck Chaubron, Chamalieres; Christian Provot, Le Cendre, both of (FR)

(73) Assignee: Genolife (FR)

(*) Notice: Subject to any disclaimer, the term of this patent is extended or adjusted under 35 U.S.C. 154(b) by 0 days.

(21) Appl. No.: 09/424,120

(22) PCT Filed: May 20, 1998

(86) PCT No.: PCT/FR98/01008

§ 371 Date: Nov. 19, 1999

§ 102(e) Date: Nov. 19, 1999

(87) PCT Pub. No.: WO98/53099

PCT Pub. Date: Nov. 26, 1998

(30) Foreign Application Priority Data

May 20, 1997 (FR) ................................................. 97 06102

(51) Int. Cl.[7] ............................ C12Q 1/68; G01N 33/53; A61K 39/40
(52) U.S. Cl. ............................ 435/6; 435/7.1; 435/183; 424/178.1
(58) Field of Search ................................. 435/6, 7.1, 183; 424/178.1

(56) References Cited

U.S. PATENT DOCUMENTS 5,705,334 * 1/1998 Lippard et al. ........................... 435/6
6,132,968 * 10/2000 Le et al. .................................. 435/6

FOREIGN PATENT DOCUMENTS

WO93/02216 * 2/1993 (WO).
WO 9623895   8/1996 (WO).
WO 9624688   8/1996 (WO).
WO 9628571   9/1996 (WO).

OTHER PUBLICATIONS

Salles et al. "A chemiluminescent microplate assay to detect DNA damage induce by genotoxic treatments" Analytical Biochemistry. 1995, 232:37–42.*

B. Salles, et al., "A Chemiluminescent Microplate Assay to Detect DNA Damage Induced by Genotoxic Treatments" Analytical Biochemestry, vol. 232, 1995, pp. 37–42.

B. Salles, et al., "In Vitro Eukaryotic DNA Excision Repair Assays; An Overview" Biochimie, vol. 77, No. 10, 1995, pp. 796–802.

P. Calsou, et al., "Double Strand Breaks in DNA Inhibit Nucleotide Excision" The Journal of Biological Chemistry, vol. 271, No. 44, 1996, pp. 27601–27607.

P. Calsou, et al., "Measurement of Damage–Specific DNA Incision by Nucleotide Excision Repair In Vitro" Biochemical and Biophysical Research Communications, vol. 202, No. 2 1994, pp. 788–795.

(List continued on next page.)

Primary Examiner—Carla J. Myers
Assistant Examiner—B J Forman
(74) Attorney, Agent, or Firm—Finnegan, Henderson, Farabow, Garrett & Dunner, L.L.P.

(57) ABSTRACT

The invention concerns a method for detecting impairment of DNA comprising contacting a sample DNA with a composition comprising at least one recognition protein selected from the group consisting of proteins belonging to the nucleotide excision repair system, proteins belonging to the base excision repair system, and proteins belonging to the system for detecting DNA breaks and detecting a complex formed between the recognition protein and DNA to thereby detect impairment of the DNA sequence.

16 Claims, 4 Drawing Sheets

OTHER PUBLICATIONS

B. Salles P. Calsou, "Rapid Quantification of DNA Repair Synthesis in Cell Extracts" Analytical Biochemistry, vol. 215, 1993, pp. 304–306.

P. Calsou and B. Salles, "Properties of Damage–Dependent DNS Incision by Nucleotide Excision Repair in Human Cell–Free Extracts" Nucleic Acids Research, vol. 22, No. 23, 1994, pp. 4937–4942.

E. Zuber, et al., "A Descriptive Model for the Kinetics of a Homogeneous Fluorometric Immunoassay" Journal of Immunoassay, vol. 18, No. 1, 1997, pp. 21–47.

R.D. Wood, et al., "Complementation of the Xeroderma Pigmentosum DAN Repair Defect in Cell–Free Extracts" Cell, vol. 53, 1988, pp. 97–106.

Sibghat–Ullah, et al., "Human Nucleotide Excision Repair in Vitro: Repair of Pyrimidine Dimers, Psoralen and Cisplatin Adducts by HeLa Cell–Free Extract" Nucleic Acids Research, vol. 17, No. 12, 1989, pp. 4471–4484.

* cited by examiner

METHOD FOR DETECTING QUALITATIVE AND QUANTITATIVE ALTERATIONS IN DNA AND LIGANDS OF SAID ALTERATION LIGANDS

This application is a 371 of PCT/FR98/01008, filed May 29, 1998.

The subject of the present invention is a method for the qualitative and quantitative detection of impairments of DeoxyriboNucleic Acid (DNA), it being possible for these impairments to be due to the metabolism of the cell or to endogenous or exogenous, physical or chemical agents, as well as a method for the qualitative and quantitative detection of the ligand(s) recognizing impaired DNA.

The most satisfactory definition (among the many which are much debated) of genotoxicity is a general definition which envisages the appearance of physical or chemical impairments of the DNA due to a direct action of the genotoxic agent or of a metabolite, as well as its biological consequences (Butterworth, 1990, Mutat. Res., 239, 117–132; Ashby, 1992, Mechanism of Carcinogenesis in risk identification, Vainio H., Magee P. N., McGregor D. B. & McMichael A. J. (eds) IARC, Lyon, 135–164). Among the genotoxic agents, many molecules or physical agents are capable of inducing the appearance of mutations which are detected by various bacterial or eukaryotic systems. The system for detecting mutagens which is most generally used is that described by B. N. Ames (Ames et al., 1973, Proc. Natl. Acad. Sci. USA, 70, 2281–2285), supplemented by the so-called micronucleus test (Mac Grégor et al., 1987, Mutat. Res., 189, 103–112).

Since mutagenesis appears to be in numerous cases the consequence of the presence of lesions (due in particular to genotoxic agents), many systemes capable of detecting and quantifying these types of damage to DNA have been developed. The detection of DNA lesions involves physico-chemical techniques such as post-labeling (Randerath et al., 1981, Proc. Natl., Acad. Sci. USA, 78, 6126–6129), alkaline or neutral elution (Kohn et al., 1976, Biochemistry, 15, 4629–4637), immunological techniques (Philips D. H., Chemical-carcinogenesis and mutagenesis, vol. I, 503–546, Springer Verlag, Heidelberg, 1990, Cooper and Grover (eds), or calls into play the consequences of events for the repair of these lesions such as the comet assay (Singh et al., 1998, Exp. Cell Res., 175, 184–191).

Some assays use the lesion-repair capacity of the cell whose mechanism involves a step of synthesis of DNA de novo. This DNA polymerization step may be quantified using radiolabeled nucleotides (Cleaver, 1984, Methods for studying excision-repair of eukaryotic DNA damaged by physical and chemical mutagens (Kilbey B. J., Nichols W. & Ramel C., eds) 33–69, Elsevier, Amsterdam). This assay has been called UDS (Unscheduled DNA Synthesis) and has been used for the detection of a genotoxic agent or for the evaluation of the repair capacities of cells. This UDS test has been improved in the sense of the non-use of a radioactive marker (Selden et al., 1994, Mutation Res., 315, 147–167) but this improvement is made relative because of the use of flow cytometry which makes the method cumbersome.

The repair of DNA is mainly due to the system for the excision of lesions, which system has been recently reproduced with cellular extracts (Wood et al., 1988, Cell, 53, 97–106; Sibghat-Ullah et al., 1989, Nucleic Acids Res., 17, 4471–4484). This assay uses treated and untreated (control) plasmids incubated in the presence of transcriptionally active extracts (Manley et al., 1983, Meth. Enzymol., 101, 568–582). The repair reaction consists in the incision-excision of the lesions and then the resynthesis of a DNA fragment. The method takes advantage of this step during which one or more radiolabeled nucleotides are incorporated. Two major mechanisms are involved in the restoration of the damage to DNA: the excision of nucleotides (NER) and the excision of bases (BER). These two mechanisms will be described later.

In the case of this test in vitro, the repair of lesions by NER involves only a small percentage of lesions, of the order of 7%.

These assays are not applicable to a large screening or, in a wider sense, industrial research application for various reasons:

(i) the number of samples which can be treated simultaneously (of the order of a few tens) is too low, (ii) the time required for the analysis (about 2 days) is relatively long, (iii) the use of radiolabeled molecules restricts this test to approved laboratories, (iv) the test is restricted to the use of highly purified plasmid DNA (supercoiled form).

Taking these constraints into account, a new in vitro repair-synthesis assay capable of overcoming the disadvantages of the other systems has been developed, by allowing the simultaneous analysis of more than 100 samples in 5 hours, with a nonradioactive detection system. This method, which also allows the use of DNA of different types, has been the subject of a French patent application No. 95 03230 of Mar. 15, 1995 and of a PCT application No. PCT/FR 96/00391 of Mar. 13, 1996, published under the No. WO 96 28571 on Sep. 19, 1996.

The object of other fairly similar techniques is the direct detection of damaged DNA, but none relates to the detection of the repair systems linked to lesioned DNA. For example, the quantitative detection of the impairments of DNA by incorporation of radioactively labeled nucleotides is described in patent applications Nos. WO 96 24688 and WO 96 23895 and in the following articles: Salles B. et al. In vitro eukaryotic DNA excision repair assays; an overview; Biochimie, vol. 77, No. 10, 1995; Calsou P. and Salles B. Measurement of Damage-specific DNA incision by nucleotide excision repair in vitro; Biochemical and Biophysical Research Communications, vol. 202, No. 2, Jul. 29, 1994; Calsou P. and Salles B. Properties of damage-dependent DNA incision by nucleotide excision repair in human cell-free extracts, Nucleic Acids Research, vol. 22, No. 23, 1994; Salles B. and Calsou P. Rapid quantification of DNA repair synthesis in cell extracts, Analytical Biochemistry, vol. 215, 304–306, 1993.

The patent application No. WO 96 24688 relates in particular to the use of anti-modified DNA antibodies and the article by Salles B. et al. (A chemiluminescent microplate assay to detect DNA damage induced by genotoxic treatments, Analytical Biochemistry, vol. 232, 37–42, 1995) relates to the incorporation of DIG-11-dUTP and the use of anti-DIG-11-dUTP antibodies for the detection of lesions.

Among the prior art documents, none describes or suggests the present invention as defined below.

DESCRIPTION OF THE INVENTION

Thus, the subject of the present invention is a method for identifying an impairment of a DNA sequence which can allow a detection of all the impairments of DNA by means of a method whose use is relatively simple.

To do this, the present invention proposes a method for identifying an impairment of a DNA sequence, characterized in that:

a) said DNA sequence is brought into contact with a composition containing at least one compound recognizing the type of impairment implicated, called a ligand, in a medium allowing the recognition, b) the recognition of the impairment by said ligand is revealed.

By recognition of the impairment by said ligand, it is understood that the direct or indirect attachment of the ligand to the damaged DNA is detected. This may be an indirect attachment when the ligand is part of a complex for example.

Impairment is understood to mean, first of all, the damage to DNA. This may be of physical origin (for example thermal, or ionizing or nonionizing radiation) or of chemical origin. These factors which damage DNA may be of exogenous or endogenous origin. The types of lesion generated on the DNA can be roughly classified into 5 types:

adducts (generally covalent formation of complex, but which may involve another type of chemical bonding such as the coordination bonding of a molecule to a base of the DNA), coupling of bases (achieved by a supply of energy, the best known type being found in the dimers of pyrimidine bases formed under the action of UVC or UVB radiation), complexing of bases of the DNA with proteins (this type of complexing, most often covalent, also being the consequence of a supply of energy), oxidative damage causing modifications of the structure of the DNA (in the form of breaks in or deletions of bases, breaks in deoxyribose, breaks in the phosphodiester bond, and the like), breaks caused by ionizing radiation (such has some types of radioactive radiation).

In addition to these types of damage, other impairments of DNA may occur. During the replication of DNA, the polymerase involved in this process has to synthesize the new strand by correctly pairing the new bases with the template strand according to the A-T, G-C model. A mismatch constitutes an impairment of the DNA. This mismatch may be natural (due to a statistical error by the polymerase) or the consequence of a drug which will disrupt the activity of the enzyme.

The method according to the present invention makes it possible to detect both the "Adamage to the DNA" and the "mismatches".

In the face of all these impairments, the cell fortunately possesses an enzymatic arsenal allowing it to restore the DNA to its normal form. These mechanisms are grouped under the general name of "DNA repair". Depending on the type of impairment, 5 principal mechanisms are involved: the excision of nucleotides, the excision of bases, the system of mismatch repair, the repair of DNA single strand breaks and the repair of DNA double strand breaks.

These mechanisms have in common the fact that they involve, in a first step, a recognition of the impairment. It is precisely by virtue of the existence of compounds, in particular proteins, which are involved in the recognition of the impairment, called hereinafter "ligands", that it has been possible to develop the method according to the present invention.

Accordingly, in a preferred embodiment of the method according to the present invention, the ligand revealed will preferably be a DNA repair system recognition protein.

"Repair system" is understood to designate both the damaged DNA repair systems and the mismatch repair systems. Finally, "recognition protein" is understood to mean both the protein ensuring primary recognition of the impairment and the protein involved in this recognition, in particular when there is formation of a complex (for example XP-A, RPA or TFIIH in particular).

Among the proteins involved, there may be mentioned:
the proteins of the NER system,
the proteins of the BER system,
the mismatch repair proteins,
the proteins of the systems detecting breaks in DNA, whether it is double or single stranded.

The nucleotide excision repair (NER) system is the mechanism recognizing the broadest spectrum of lesions on DNA, these lesions consisting mainly of cumbersome adducts.

NER repair is conventionally separated into 4 stages: recognition of the lesion (1); excision of the lesion (2); resynthesis of the excised fragment (3); ligation of the newly-synthesized strand (4).

The mechanism of recognition of the lesions repaired by NER is not yet clearly defined but it is, on the other hand, clearly established that the XP-A protein is involved (in association or otherwise with the RPA protein and optionally the transcriptional complex TFIIH) in one of the first recognition stages.

XP-A is the protein in which Xeroderma pigmentosum group A patients are deficient. The absence of an NER repair protein makes these patients very sensitive to UV radiation which, depending on the wavelength, generates on the DNA damage repaired by NER, the XP-A form being the most severe form.

The XP-A protein is a zinc finger protein (conventional structure of proteins interacting with DNA) consisting of 273 amino acids and translated from a messenger RNA of 1.4 kb (Tanaka K. et al., 1990, Nature, 348, 73–76).

XP-A recognizes (with a preference of a factor of 1000 relative to a nonlesioned DNA) the damage generated by UVC (about 75% of pyrimidine dimers in cyclobutane form, 25% of pyrimidine dimers in the form of photoproducts (6–4)). Only these types of lesions were analyzed in that study (Robins P. et al., 1990, EMBO J., 10, 3913–3921). These authors also generated polyclonal antibodies against two synthetic peptides of the XP-A protein and determined that the XP-A protein does not require phosphorylation in order to be active.

Using chromatography columns consisting either of agarose coupled to single-stranded DNA or cellulose coupled to DNA irradiated with UVC, or by incubating various types of DNA (single- or double-stranded, lesioned with UVC or otherwise), Eker et al. concluded that the XP-A protein extracted from calf thymus or from the HeLa cells exhibits a higher affinity for single-stranded DNA than for double-stranded DNA, but no preference for DNA lesioned with UVC (Eker et al., 1992, Mutation Res., DNA, 274, 211–224). These authors also generated polyclonal antibodies against the recombinant XP-A proteins.

The results obtained by Tanaka et al. were completed in 1993 with the aid of a recombinant XP-A protein. It was confirmed that XP-A indeed recognizes the UVC lesions and mainly the photoproducts (6–4), as well as the lesions due to the antitumor agent cisplatin (cis-diamine-dichloroplatinum (II)). A single-stranded DNA fragment is four times more effective in a competition toward a UVC-lesioned DNA with respect to XP-A than a double-stranded DNA. On the other hand, these authors were not able to demonstrate affinity of XPA toward a DNA containing adducts derived from photoactivated psoralen (Jones C. J. & Wood R. D., 1993, Biochemistry, 32, 12096–12104).

To the knowledge on the lesions due to UVC as well as those due to cisplatin, Asahina et al. added in 1994 the lesions due to osmium tetroxide (Asahina H. et al., 1994, Mutation Res., DNA Repair, 315, 229–237).

The cloning of the genes encoding XP-A in chicken, xenopus and drosophila (in which it has been called Dxpa) shows a high conservation of these genes from evolution in eukaryotes (T. Shimamoto et al., 1995, J. Biol. Chem., 270, 22452–22459).

The excision of bases appears to be normal in XP cells (Cleaver J. E. & Kraemer K. H., 1989, The metabolic basis of inherited disease, ed. Scriver C. R., Beaudet A. L., Sly W. S. & Valle D. (McGraw-Hill, New York), 6th Ed., 2949–2971), which confers on XP-A the specificity of recognition of the lesions repaired by NER. However, using DNAs lesioned by γ radiation or by the hydroxyl radicals generated by decomposition of hydrogen peroxide, treated so as to no longer be recognized by the base excision repair system, Satoh et al. show the involvement of XP-A (as well as XP-B and XP-C, two other subgroups of Xerodermat pigmentosum which contains seven such groups called XP-A to XP-G), in the repair of some classes of lesions induced by oxygenated free radicals (Satoh M. S. et al., 1993, Proc. Natl. Acad. Sci. USA, 90, 6335–6339). The type of substrate used to demonstrate the involvement of proteins of the XP group in this repair process being completely artificial, these results should be taken with care.

Finally, it has been shown by the double hybrid technique or by more conventional immunological techniques that the XP-A protein (recombinant) binds to the RPA protein (Replication Protein A, also called Human Single-Stranded DNA Binding protein, HSSB). It has however not been shown in these experiments that this association was involved in nucleotide excision repair (Matsuda T., 1995, J. Biol. Chem. 270, 21800–21805).

The potential role of the HMG (High Mobility Group) proteins should be added. These proteins become involved during lesions caused by cisplatin, an agent used in chemotherapy (Hughes et al., 1992, J. Biol. Chem. 267; 13520–13527). Four HeLaS3 proteins specific for the adducts caused by cisplatin have been identified (Donahue et al., 1990, Biochemistry, 29, 587–5880; Andrews and Jones, 1991, Cancer Comn. 3, 1–10; Hughes et al., 1992, J. Biol. Chem., 267, 13520–13527). The sequencing of the N-terminal part of two of these proteins revealed a strong homology with the HMG2 and HMG1 proteins. Likewise, the covalent bonding of a chromium salt to DNA induces adducts recognized by HMG1 and HMG2 in vivo. The affinity of the HMGs is dose-dependent with respect to the chromium salt (Wang et al., 1997, Carcinogenesis, 18, 371–375).

However, their exact role in DNA repair has not yet been established (no recognition in particular of lesions caused by UV).

In carrying out the method according to the present invention, the revealing of the XP-A protein or of related proteins as well as optionally the RPA, TFIIH and HMG proteins or of other proteins of the complex will preferably be used.

Depending on the nature of the ligand detected, it will be possible, in addition, to envisage defining better the type of genotoxic agent implicated. Indeed, XP-A recognizes voluminous adducts and corresponds to numerous genotoxic agents but does not recognize nonvoluminous adducts and oxidative bonds.

Base excision repair (BER) is less well known than nucleotide excision repair (NER). The main reason lies in the absence of mutants which can serve for the search for genes involved in this mechanism since no disease exists which is identified as resulting from a BER deficiency.

Base excision repair is used on the DNA bases lesioned by endogenous oxygenated reactive species, ionizing radiation and alkylating agents. To simplify, BER is used on damage which is not very voluminous unlike NER which recognizes voluminous damage.

The key enzymes in BER are glycosylases which remove the modified bases by cleaving the N-glycoside bond between the base and the deoxyribose. Different glycosylases exist which recognize different types of damage. To date, about ten of these enzymes have been identified in *Escherichia coli, Saccharomyces cerevisiae* and in humans (Seeberg et al., 1995, TIBS, 20, 391–397).

Once the base has been removed, the AP (purine-free or pyrimidine-free) site is excised by an AP-endonuclease or an AP-lyase which cleave the DNA strand on the 5' or 3' side, respectively, of the AP site. The remaining deoxyribose-phosphate is excised by a phosphodiesterase and the resynthesis of the DNA strand is restored by a DNA polymerase. The continuity of the strand is then restored by a DNA ligase.

It has been accepted for a long time that β-polymerase was involved in the resynthesis of the DNA strand in BER. Now, it has recently been shown on hamster (CHO) cell extracts that 2 different mechanisms can repair small adducts due to alkylating agents. One involves β-polymerase, the other exhibits some similarities with NER since it calls into play PCNA (Proliferating Cell Nuclear Antigen; a factor involved in NER) (Frosina et al., 1996, J. Biol. Chem., 271, 9573–9578). The damage to DNA due to UVA is probably repaired by BER. Indeed, cells of an XP-D line show no difference in behavior, compared with a wild-type line, in terms of survival curve following UVA irradiation (320–410 nm) whose damage is of the oxidative type, and therefore repaired by BER, whereas they are hypersensitive to UVB (307–312 nm) and UVC (254 nm) (Stary et al., 1997, Mutation Res., 383, 1–8).

Poly(ADP-ribose) polymerase, or PARP, which is involved in the repair of single-strand breaks is also involved in the final step of ligation of the repair by BER (Kubota et al., 1996, EMBO J. 15, 6662–6670).

Base mismatches may occur during replication, recombination or following damage to DNA.

The mechanism of mismatch repair is well known in the *E. coli* bacterium. The MutHLS system has thus been reconstituted in vitro: it is composed of the MutH, MutL, MutS and UvrD (or helicase II) proteins. The mechanism is complemented by DNA polymerase III, DNA ligase and SSB (Single-Stranded DNA Binding protein) and a single-strand specific exonuclease (Exo I, Exo VII or the RecJ protein (Friedberg et al., 1995, DNA repair and Mutagenesis, ASM Press).

The MutS protein recognizes the mismatch and MutH is an endonuclease. No activity has yet been attributed to MutL, although it interacts with MutS and is necessary for the activation of MutH.

Several data appear to show that the homolog of the MutHLS system exists in humans, in particular the purification of homologs to MutL (called hMLH1) and MutS (called hMSH2). hMSH2 recognizes both the single base mismatches (like MutS) but also more complex. mismatches due to multiple deletions/insertions (Fishel et al., 1994, Science, 266, 1403–1405; Alani et al., 1995, Genes Dev., 9, 234–247). It has furthermore been recently shown that hMSH2 may be copurified with a protein of 160 kD, called GTBP (G/T Binding Protein) (Drummond et al., 1995, Science, 268, 1909–1912; Palombo et al., 1995, Science, 268, 1912–1914), but the role of these GTBPs is not clearly elucidated. Likewise, hMLH1 appears to be associated with another protein, hPMS2, and to form a heterodimer called hmutLα (Li & Modrich, 1995, Proc. Natl. Acad. Sci. USA, 92, 1950–1954).

A deficiency in this mismatch repair mechanism is clearly correlated with a predisposition to cancers, in particular to hereditary nonpolyposis colon cancer (HNPCC). This is the case during mutations of hMSH2 (Fishel et al., 1993, Cell, 75, 1027–1038; Leach et al., 1993, Cell, 75, 1215–1225) or of hMLH1 (Bronner et al., 1994, Nature, 368, 258–261; Papadopoulos et al., 1994, Science, 263, 1625–1629).

The Mut proteins, in particular MutS or HMSH2, contain the best targets for carrying out the method according to the present invention.

The importance of the search for this type of ligand lies in the characterization of cell extracts (biopsy or directly in vivo). Indeed, a deficiency in rhe HMSH2 system is in general associated with an increased risk of development of cancers.

The damage to DNA of the single-strand break type may be induced by alkylating agents or ionizing radiation. These breaks are immediately recognized in the cell by poly(ADP-ribose) polymerase, or PARP.

This enzyme is present in a very large quantity (of the order of a million molecules) in the nuclei of eukaryotic cells (with the exception of yeast).

The study of the nucleotide sequence has shown that this protein has 2 domains, an N-terminal domain containing 2 zinc fingers and binding to DNA, and a C-terminal domain having a catalytic function (Cherney et al., 1987, Proc. Natl. Acad. Sci. USA, 84, 8370–8374).

The cleavage is recognized by covering 7–8 nucleotides on each side of the cleavage (Gradwohl et al., 1990, Proc. Natl. Acad. Sci. USA, 87, 2990–2994).

When it binds to a DNA single strand cleavage, the catalytic activity of PARP is activated. PARP produces poly(ADP-ribose) using, as substrate, nicotin-amide adenine dinucleotide (NAD).

The lifespan of the poly(ADP-ribose) chain is normally very short, of the order of a few minutes. It is possible to block the reaction at the DNA-PARP interaction stage by inhibiting the synthesis of poly(ADP-ribose) with the aid of a structural analog of NAD. 3-aminobenzamide (Prigent et al., 1994, Mol. Cell. Biol., 14, 310–317).

PARP does not participate in DNA repair but protects the break from endonucleases. It has in particular been shown that PARP does not play a role in the NER mechanism (Molinette et al., 1993, EMBO J., 12, 2109–2117; Aboussekhra et al., 1995, Cell, 80, 859–868).

While a role in the recognition of DNA single strand breaks is well established for PARP, its physiological role is less clear. It has been proposed that it could, for example, have a role in triggering apoptosis, by various pathways, but in particular by exhausting the cellular stock of NAD. PARP could protect the genomic stability of the cell by avoiding excessively frequent recombination events at the break sites. It could also play a role in the opening of regions of chromatin by interfering with the histones (review by Lindahl et al., 1995, TIBS, 20, 405–411).

The DNA double strand breaks are created in particular by ionizing radiation, but may result from an endogenous origin as in some recombination reactions.

The poor repair or the absence of repair of these lesions may be highly deleterious because it can cause deletions or translocations having as possible consequences the inactivation of a gene.

In mammals, 4 complementation groups have been identified for the repair of double strand breaks, defining 4 genes involved in this process (review byd Jackson & Jeggo, 1995, TIBS, 20, 412–415). Among these 4 groups (IR4–7; IR for ionizing radiation), the IR5 and IR7 groups, whose products are XRCC5 and XRCC7 (X-ray Repair Cross-Complementing) are more particularly of interest to us.

The IR5 and IR7 groups are deficient in the constituents of DNA-PK. DNA-PK (DNA-dependent protein kinase) is a serine/threonine kinase which is only active when it is bound to DNA (the similarity with PARP may be noted in passing) (Getts & Stamato, 1994, J. Biol. Chem., 269, 15981–15984; Rathmell & Chu, 1994, Proc. Natl. Acad. Sci. USA, 91, 7623–7627; Taccioli et al., 1994, Science, 265, 1442–1445). DNA-PK consists of a catalytic subunit (DNA-PK$_{cs}$) and a subunit interacting with DNA called Ku.

Ku, originally identified as an autoantigen, is a heterodimer consisting of 2 polypeptides of 70 and 80 kDa (Ku70 and Xu80) and corresponds to XRCC5. It binds to the ends of DNA but not to cellular DNA (Gottlieb & Jackson, 1993, Cell 72, 131–142) and thus activates the DNA-PKR$_{cs}$ subunit.

Apart from the inactivation by phosphorylation of RNA polymerase I in the vicinity of the DNA breaks (Kuhn et al., 1995, Genes Dev., 9, 193–203), the substrates of DNA-PK$_{cs}$ (encoded by XRCC7) are not yet well defined and its role in DNA repair remains to be proven.

The Ku ligand used for employing the double strand breaks can be more particularly be used for the identification of ionizing radiation (nuclear power stations or hospitals, for example).

As has been just described, while the DNA repair mechanisms are not always known in detail, it is known that the impairments of DNA are first of all recognized by very precise ligands or by recognition proteins, this recognition preceding the repair stage designed to reconstitute the DNA in its actual form. It is advantageous to note, for example, that while in the case of repair by NER only 7% of the lesions are repaired in vitro, the majority of the lesions, if not all, are recognized since they all induce deformation of the DNA and since it is the actual repair step which is limiting.

Accordingly, the method according to the invention uses the observation that in an in vitro system, most of the impairments, even if they are not repaired, are nevertheless recognized and that this recognition step should be used for the identification of the impairments.

The method according to the invention is therefore based on the detection of the interaction of one or more molecules of the repair systems which recognize impairments of DNA, in particular the proteins.

The method according to the present invention is first of all a qualitative method, that is to say that it makes it possible to detect the existence of an impairment of DNA and its nature as a function precisely of the type of ligand. Thus, the identification of an interaction of XP-A with the DNA shows an impairment calling into play NER; by contrast, the interaction of MutS or HMSH2 demonstrates a problem of mismatch. This type of test makes it possible in particular to define the genotoxicity of a medium and the nature of the action on DNA.

However, it may be quantitative if the quantity of ligand bound can be quantified, for example with respect to standards. In the latter case, it will thus be possible to evaluate the importance of the impairment and to monitor its changes. In this case in particular, it will be possible to classify, for example, the genotoxic agents as a function of their genotoxicity, but also to monitor the change in an impairment over time, for example in order to "monitor" a treatment.

In the tests described above, the product tested is a DNA which has been impaired by a genotoxic agent whose activity it is desired to evaluate. It is also possible to use the method according to the invention to measure, starting somewhat from a "known determined impairment of DNA", the activity of a repair system.

In particular, it is possible to envisage the identification of a deficiency in certain repair systems.

Indeed, in the method according to the present invention, in order to ensure the conditions for recognition, it is necessary to provide, in addition to the ligand, for the presence in the medium of other elements ensuring the recognition, cofactors in particular; to do this, a cellular extract which may provide the ligand or otherwise (in this case the ligand will be added) will be used in general.

When it is desired to test a possible deficiency of a repair system of certain cells (biological samples for example), it will be possible to use an extract of these cells to test it directly on an impaired DNA, it being possible for the impairment recognition activity to be evaluated by a standard prepared, for example, with a normal cell extract.

Accordingly, the present invention also relates to a method allowing the identification, in a sample, of an impairment of the DNA repair system, characterized in that:

a) the sample is brought into contact with an impaired DNA, b) the recognition of the impairment by a ligand of the repair system is revealed, c) the result obtained in step b) is evaluated relative to a standard.

It can be seen that all the developments made on the principal method can also be used in the method described above.

The standard may be, for example, a normal sample treated under equivalent conditions or any other method, in particular calibration curves.

"Impairment of the repair system" is understood to mean any modification of the response in the preceding test of a repair system relative to a control system serving as standard. This impairment will be characterized in general by a deficiency in the recognition of the impaired DNA, but the opposite is also possible.

Thus, it will be possible for the method according to the invention to allow the identification of the presence or the absence of proteins in relation, for example, to a determined pathology. Such an application may be exploited for evaluating the acquired resistance to certain alkylating agents used in antitumor treatment in patients by measuring a deficiency in mismatch repair (Eshlemen & Markowitz, 1995, Curr. Opin. Oncol. 7, 83–89) or the sensitivity or resistance to radiotherapy.

Furthermore, this same method according to the invention makes it possible to identify impairments in the modulators of recognition of DNA ligands (such as antitumor agents interacting with repair factors).

Indeed, in this case, modifications will be noted in the response of the recognition ligands.

The specific use of the method according to the present invention may be carried out according to different variants.

The method according to the present invention may be used according to different variants.

The DNA tested may be a total cell extract, a semipurified cell extract or alternatively a purified DNA; this will depend on the type of research carried out.

The recognition medium may be completely synthetic or alternatively may consist of a cell extract, which may in particular also contain the ligand; in this case, the revealing will be carried out with a marker for the binding of the ligand, a labeled antibody for example. In any case, the recognition medium should contain all the cofactors necessary for the recognition of the impairment.

Preferably, the recognition medium consists of a cell extract which is purified to a greater or lesser degree with respect to the presence of a ligand which is endogenous and of DNA which is endogenous to said recognition medium.

The interaction of the ligand and of the DNA may be detected by any appropriate method, in particular as has been specified, with the aid of a labeled ligand or with the aid of an antibody recognizing the ligand.

In all cases, the labeling may be radioactive or otherwise. The use of nonradioactive labeling, that is to say fluorescent labeling for example, or of enzymatic labeling will be preferred.

In particular, it is possible to envisage that step a) comprises compounds recognizing different types of impairment and that in step b) the different types of recognition can be identified separately. In the case of fluorescent markers, it will thus be possible to use different chromophores. This makes it possible to immediately visualize the type of impairment or even the various impairments.

More specifically, the method comprises the following steps:

the action, in the case of the use of a target DNA, of the agent (physical or chemical) to be tested on this DNA; in the case of a chemical agent, the action of the compound may require the concomitant action of a mixture for activating the compounds (such as for example a bioconverting action of a type "S9" hepatic extract in the presence of all the necessary cofactors);

the purification of DNA of cells or tissues for which it is desired to know the degree of impairment of the DNA (for example monitoring of patients or people in contact with risky environments, incubation of cells in culture with agents whose genotoxicity is to be determined; search for correlation between the state of impairment of the cellular DNA and the presence of or predisposition to certain diseases, for example);

the action of a cell extract possessing a repair activity, or at least an impairment recognition activity, on this DNA, or more simply of a protein, or protein complex, recognizing these impairments or an extract deficient in a protein which will be added;

the revealing of the interaction of a protein or protein complex with the aid of an antibody; more simply, in the case of a purified protein recognizing the lesions, it is possible to directly graft on this protein a direct revealing marker (of the fluorescence type for example) or an indirect revealing marker (of the enzymatic type), these examples not being limiting;

in the case of the use of an antibody, its direct or indirect revealing (directly labeled antibody) or its revealing with a secondary antibody (or ligand);

detection preferably chosen from the sensitive techniques such as luminescence (luminescent substrate) or fluorescence, optionally radioactivity.

All these steps may be carried out in a liquid phase or in a semisolid phase by attaching one of the reagents to a support (microtiter plate, membrane or microbead, gel, or agarose column or affinity column, for example); in the first case, a system will be preferably chosen which does not require washings between the different steps or which is a single-step system; in the second case, the different steps are separated by washing.

In the case of an assay with a solid or semisolid phase, the nature of the reagent attached, ligand or DNA in particular, may depend on the type of assay carried out, assay of the extent of the lesion or alternatively assay of the recognition.

In the case of an assay in a liquid phase, it is necessary to be able to detect the attachment of the ligand to the DNA; it is possible in particular to envisage two different labelings for the DNA and the ligand and to visually evaluate the proximity of the markers; it is also possible to use TRACE type systems in which one of the markers can only be revealed by the proximity of the second. In general, the test consists in incubating the DNA (lesioned or otherwise) both in the presence of an anti-DNA antibody and of a protein specific for impairments of the DNA. Said protein may be coupled directly to a fluorophore or may be revealed by an antibody. In the case of the use of an anti-DNA antibody and of a specific protein, each of the two ligands may be coupled to a fluorophore whose emission wavelengths are sufficiently different to be simultaneously read with good discrimination. It is also possible, in both cases. envisaged above, to use a TRACE™ (Time-Resolved Amplified Cryptate Emission) detection system described by CIS Bio International (Bagnols-sur-Sèze, France). It. would be possible, in this case, to conjugate the anti-DNA antibody with "cryptate" (Europium trisbipyridinediamine) and to bind a lesion recognition protein or the antibody recognizing it to an energy-accepting fluorophore such as the modified phycobiliprotein, called XL665 by CIS Bio International (or the opposite), or to label 2 proteins which only form a complex in the vicinity of the impaired DNA. It is possible to envisage standardizing the reading by expressing the signal in terms of the quantity of DNA. This quantity of DNA (relative) may be obtained with the aid of the same system using, for example, two anti-DNA antibodies, one coupled to cryptate, the other to the energy-accepting fluorophore.

The advantage of the TRACE™ system is its speed (since it is not necessary to carry out washing steps), but especially the quantity of DNA (and therefore of lesions) which can be analyzed per condition. Furthermore, this system is fully automatable, and is in fact already suitable for HTS screening.

If no purified ligand for impairment is available, or if it requires protein or nonprotein cofactors, for the interaction step, it is possible in this case to use a purified cell extract so that these cofactors are present. In this case, the interaction of the ligand with the impairment will be detected with the aid of an antibody directed against this ligand. This antibody may be coupled to a system allowing it to be detected, or a method known to persons skilled in the art is used which consists in using a second antibody directed against the first, the second antibody being coupled to a detection system.

In the solid phase assay, it will be possible to attach the damaged DNA to a support and to reveal the attachment of a ligand to the attached DNA for example; other methods may be envisaged which are derived from the methods described above for the liquid phase.

It is also possible to use assay systems of the "biochips" type, in particular the techniques developed by Affymetrix or CIS Bio International (Bagnols-sur-Sèze, France).

It is possible to envisage attaching the DNA to chips:
An oligonucleotide or DNA containing a mismatch can make it possible to detect the presence of hMSH2 in a biopsy or in vivo, and therefore the risk of developing a cancer. This method should be quantitative in order to discriminate between healthy individuals who are homozygous from those who are heterozygous for the hMSH2 gene, who are predisposed to developing cancers, in particular colon cancer.

An oligonucleotide or DNA containing an adduct of a genotoxic agent used in chemotherapy (alkylating agent, cisplatin, and the like) may be used for monitoring the level of XPA proteins and for monitoring a certain type of resistance.

It is also possible to envisage the attachment of the protein to chips:
it is no longer a question of using anti-protein antibodies but the proteins themselves. It is possible in theory, starting with this system, to detect all types of lesion and the quantification of the DNA would be carried out using an anti-DNA antibody which would make it possible to express the signal obtained for each type of lesion in terms of a "DNA" signal. This system appears to be fairly advantageous for therapeutic monitoring.

As has been described in the preamble, the method according to the present invention can be more particularly used for evaluating the genotoxicity of an environment on a sample by measuring the impairment of the DNA of said sample.

"Environment" is understood to mean chemical, biological as well as physical factors (radiation for example).

The invention is in particular applicable to a qualitative and quantitative evaluation of lesions on the DNA of cells cultured in vitro, isolated ex vivo or derived from animal or plant tissues, for example application to the detection of genotoxic xenobiotics, to the therapeutic monitoring of patients with tumors undergoing a chemotherapy treatment, application to the monitoring of risks to people in contact with potentially genotoxic agents.

It is also possible to use it, in general, for the qualitative and quantitative evaluation of compounds which react with nucleophilic molecules (DNA, lipid compounds, and the like) such as free radicals, in particular in the field of cosmetics for example, as well as for the qualitative and quantitative evaluation of compounds inhibiting the action of oxidizing agents.

Finally, the method allows the determination of the capacities of a cell extract to recognize lesions as well as the determination of the type of lesions induced on DNA by virtue of the use of either cell extracts deficient in part of the system for repairing these lesions, or specific proteins, or antibodies directed against specific proteins.

The present method, which is based on the detection of a specific interaction of proteins involved in the repair of lesioned DNA, have many advantages:
this test, in the case of a solid support, is a simple ELISA, and as such is automatable and is suitable for "high throughput screening" or HTS,
this test is all the more automatable in its completely liquid phase version,
compared in particular with the test described in French patent No. 95 03230 of Mar. 15, 1995, published on Sep. 20, 1996 under No. 2,731,711; application PCT/FR 96/00391 of Mar. 13, 1996, in reference on Sep. 19, 1996 under No. WO 96 28571, it is advantageous because
it requires less cell extracts or
it does not require cell extracts, a (or a combination of) purified protein(s) or even protein(s) produced by genetic engineering being sufficient, it does not require a modified or labeled nucleotide, for example a radioactively labeled nucleotide, it does not require adsorption of DNA onto a sensitized support, but the attachment of the target DNA may, for example, be done at one end (example: biotinylated DNA, support coupled to a biotin ligand such as streptavidin);

it is more rapid (since it only calls into play the step of recognition of the lesion and not the recognition-repair combination), which can reduce the test to a time of the order of 2 to 3 hours;

if an NER protein is used, it is possible to incubate the target DNA in the presence of an activating system: it being possible to use various sources of activating fractions:

rat or guinea pig liver S9 or microsomal fraction, induced or otherwise, extract of human HepG2 cells, stimulated or otherwise with hydrocortisone 21-hemisuccinate and benzanthracene, extract of cells of the human MCL 5 line (company Gentest), extract of recombinant eukaryotic cells expressing P450s, catalysis by porphyrins.

In the case of the use of a single recognition protein (carrying a marker or otherwise), the XP-A protein would be preferably used because it is the first to recognize a DNA lesion. Furthermore, this protein, whose complementary DNA is cloned, may be expressed in a vector propagated in a microorganism and may thus be produced in a large quantity in a fermenter, for example.

It is also possible to coincubate the XP-A protein and the RPA complex.

It is also possible to envisage using in the same manner only XPA or the RPA complex.

It is also possible to envisage using in the same manner the HMG proteins.

In general, the most advantageous systems according to the present invention are the NER and BER systems.

For the remainder of the description, reference will be made to the legend to the figures.

BRIEF DESCRIPTION OF THE DRAWINGS

1-adsorption of the target DNA onto a support 2-generation of lesions by incubation with a genotoxic agent, 3-recognition of the lesions by a protein derived from a cell extract, 4-revealing of the attachment of this protein by an antibody, 5-revealing of the attachment of the first antibody by an anti-antibody coupled to an enzyme, 6-generation of a light signal by addition of a chemiluminescent substrate of the enzyme.

The DNA is represented by a double helix, the lesions by black circles, the lesion recognition proteins by white ovals, and the antibodies coupled to an enzyme carry a white rectangle.

The whole of this test is preferably carried out at 30° C. Each step is separated by washings.

The target DNA is adsorbed onto wells preiously covered with polylysine. This DNA is subjected, or the desired duration, preferably 30 minutes, to the action of genotoxic agents or of a composition containing at least one such agent.

This step has the effect of generating lesions on the DNA, if the solution tested contains one (or more) genotoxic agent(s).

A cell extract, preferably of human origin, preferably derived from HeLa cells, is incubated over the DNA. The proteins for recognition of the impairments of the DNA will attach to the sites of impairment.

An antibody, polyclonal or preferably monoclonal, is directed against the protein for recognition of the impairments is added and will recognize the proteins attached to the sites of impairment.

A second antibody, directed against the first antibody (preferably recognizing the species from which the first antibody is derived), coupled to an enzyme, preferably of the peroxidase type, is added and will recognize the first antibody.

A luminescent substrate of the enzyme is added and the light signal emitted is quantified by a luminometer.

Figure 1:
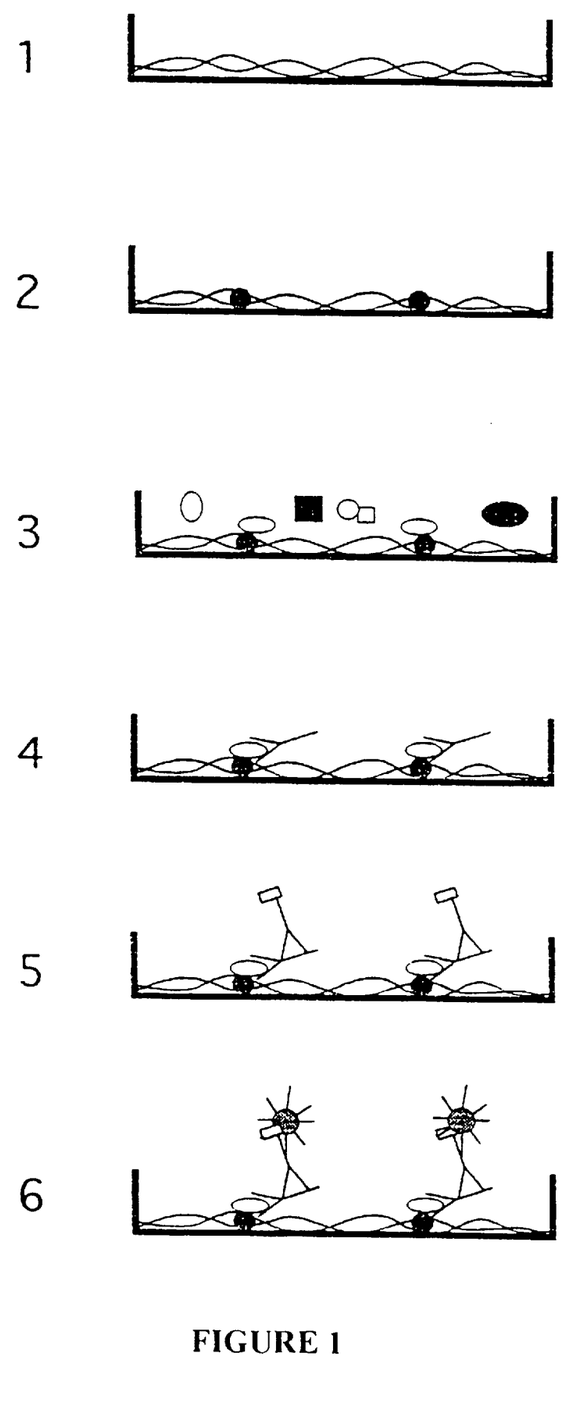
FIG. 1: Principle of the GeneTEX™ (Gene Toxicology Environment Xenobiotics) test The GeneTEX™ test comprises 6 steps.

One of the aspects of the geneTEX test is illustrated in FIG. 1. However, this test is not limited to this aspect and may comprise the following variants:

1) The antibody directed against the recognition protein may be directly coupled to a detection system, therefore not requiring a secondary antibody. This detection system may be an enzyme, a fluorescent marker, a time-resolved fluroescence marker (of the Europium chelate type) or an electrochemiluminescence marker.

2) Cells are incubated in the presence of the genotoxic agent for the desired period, and then lysed and the cellular DNA adsorbed on the sensitized wells. The whole test is then carried out normally.

3) The whole test may be carried out in a liquid phase, without the use of a solid support by using the TRACE technology developed by CIS Bio International (Bagnols-sur-Sèze, France) which uses a transfer of energy between a Europium cryptate and an energy acceptor (in particular the molecule XL665) There is emission of signal only in the case where the 2 molecules, carried for example by 2 antibodies, are sufficiently close. In the case of the test, the antibody directed against the protein for recognition of the impairment is for example coupled to cryptate, and an anti-DNA antibody is coupled to XL665 (or the reverse), or 2 antibodies directed against 2 proteins forming a complex in the vicinity of the impaired DNA are used. The 2 antibodies being sufficiently close, the transfer of energy between the excited Europium cryptate and the XL665 acceptor will be possible and the fluorescent signal emitted is proportional to the amount of antibody attached to the protein for recognition of the impairments.

EXAMPLE 1

Detection of Lesions on DNA which are Recognized by the NER System

The DNA (plasmid pUC18), at the concentration of 50 µg/ml, was lesioned with UVC by irradiation under a lamp illuminating at 254 nm at 50 µW/cm$^2$ for the time required for the production of doses varying from 5 to 200 J/m$^2$.

The DNA, prelesioned with UVC, was adsorbed onto wells coated with polylysine at the rate of 50 ng per well. As a control, DNAs carrying oxidative lesions (lesions generated by illumination in the presence of methylene blue), repaired by the BER system were used.

After incubating for 30 minutes, the wells were washed twice with a PBS solution supplemented with Tween-20 at 0.1%.

The wells were then washed twice with a PBS solution supplemented with Tween-20 at 0.1%.

The wells were then saturated with the aid of a solution of BSA at 3% in PBS for 1 hour at 30° C., with stirring.

The wells were then washed once with a PBS solution supplemented with Tween-20 at 0.1%.

The DNA treated was then incubated with a cell extract of the Manley type [Manley et al. (1980) Proc. Natl. Acad. Sci. USA, 77, 3855–3859], modified by Wood [Wood et al. (1988) Cell, 53, 97–106] for 90 minutes at 30° C. in a buffer containing 40 mM Hepes; 5 mM MgCl$_2$; 50 mM KCl; 0.5 mM DTT; 10 mM phosphocreatine; 0.1 mg/ml BSA; 50 µg/ml creatine phosphokinase; 2 mM EGTA, pH 7.6.

The wells were then washed twice with a PBS solution supplemented with Tween-20 at 0.1%.

The attachment of the XPA protein was revealed by incubating an anti-XPA monoclonal antibody diluted to 900 ng/ml in PBS supplemented with 0.1% BSA and Igepal CA-630 (sold by Sigma) for 2 hours at 30° C., with stirring.

The wells were then washed three times with a PBS solution supplemented with Tween-20 at 0.1%.

The primary anti-XPA antibody was then recognized by a secondary goat anti-mouse antibody coupled to peroxidase, diluted 1/10,000 in the same buffer as the primary antibody in an incubation of 30 minutes.

The wells were then washed five times with a PBS solution supplemented with Tween-20 at 0.1%.

A luminescent peroxidase substrate (Specichrom, sold by Speci, Ste Foy-les-Lyon, France) is then added and the whole was incubated for 15 minutes at 30° C., with stirring.

The light signal emitted was measured by a Victor (Wallac OY, Turku, Finland).

Figure 2:
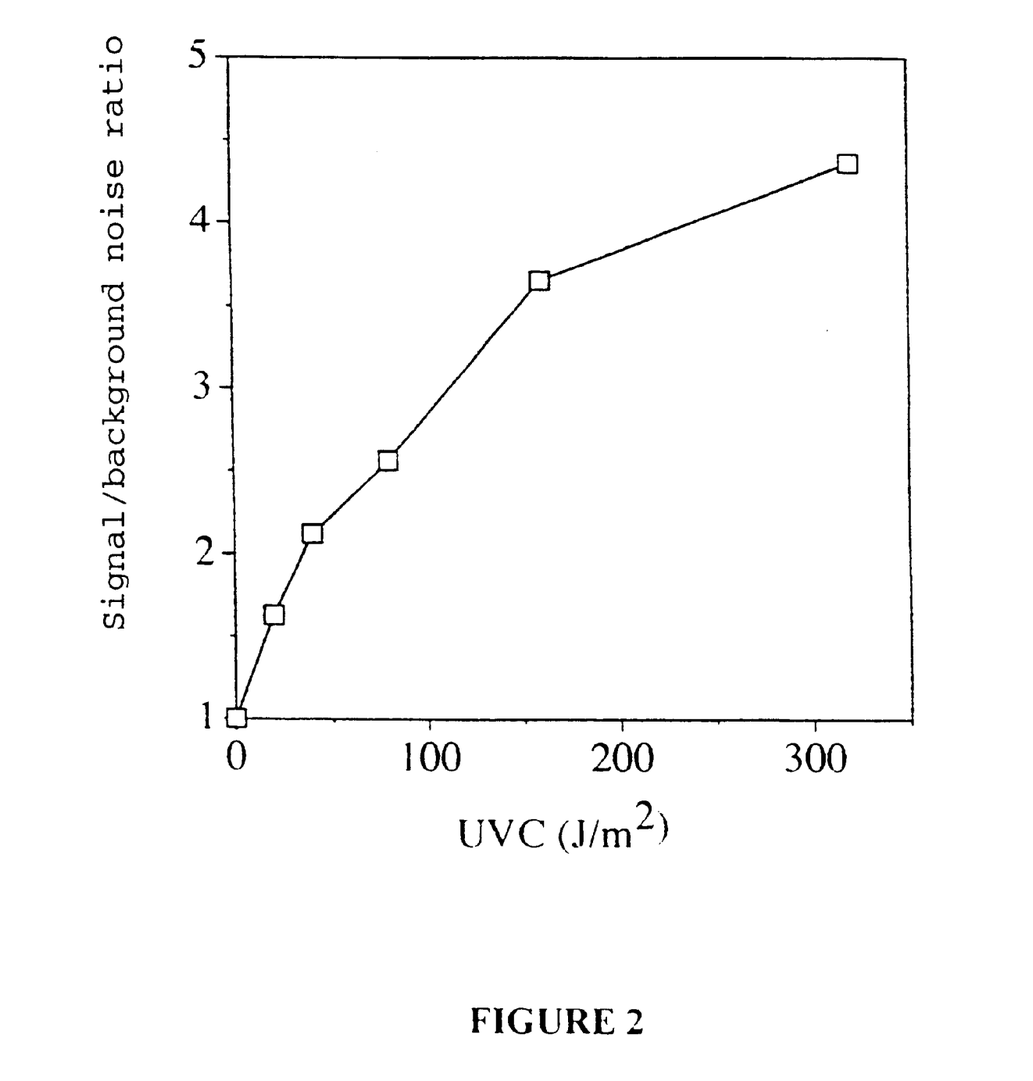
FIG. 2: Recognition of the damage due to UVC by the XPA protein in a cell extract and detection by an anti-XPA monoclonal antibody This graph represents the signal obtained (signal/background noise ratio) as a function of increasing UVC doses.

The result is expressed as the ratio of the specific signal to the untreated plasmid signal and an example of a result is given in FIG. 2.

There is thus shown at this stage of development of the test, a detection threshold of 30 J/m$^2$ for the UVC lesions.

The lesions generated by illuminated methylene blue were not detected.

EXAMPLE 2

Detection of Double Strand Breaks in DNA

This type of breaks, generating an increase in the number of DNA fragments and therefore of ends, is detected by the Ku-DNA$^{PK}$ complex. The attachment to the ends is ensured by the Ku subunit (Ku70–Ku80).

In practice, the double strand breaks were generated by a radiomimetic molecule, bleomycin, in the presence of ferrous ions: there is, in this case, production of double strand breaks as in the case of treatment with ionizing radiation.

The DNA (plasmid pUC18) was adsorbed onto wells coated with polylysine at a rate of 50 ng per well.

After incubating for 30 minutes, the wells were washed twice with a PBS solution supplemented with Tween-20 at 0.1%.

Increasing doses of bleomycin (from 0 to 200 µM) were incubated for 30 minutes with the adsorbed DNA, in the presence of 0.5 µM FeCl$_2$, with stirring at 30° C.

The wells were then washed twice with a PBS solution supplemented with Tween-20 at 0.1%.

The wells were then saturated with the aid of a solution of BSA at 3% in PBS for 1 hour at 30° C., with stirring.

The wells were then washed once with a PBS solution supplemented with Tween-20 at 0.1%.

The DNA treated was then incubated with a cell extract of the Manley type [Manley et al. (1980) Proc. Natl. Acad. Sci. USA, 77, 3855–3859], modified by Wood [Wood et al. (1988) Cell, 53, 97–106] for 90 minutes at 30° C. in a buffer containing 40 mM Hepes; 5 mM MgCl$_2$; 50 mM KCl; 0.5 mM DTT; 10 mM phosphocreatine; 0.1 mg/ml BSA; 50 µg/ml creatine phosphokinase; 2 mM EGTA, pH 7.6.

The wells were then washed twice with a PBS solution supplemented with Tween-20 at 0.1%.

The attachment of the Ku complex was revealed by incubating an anti-Ku monoclonal antibody diluted to 400 ng/ml in PBS supplemented with 0.1% BSA and Igepal CA-630 (sold by Sigma) for 2 hours at 30° C., with stirring.

The wells were then washed three times with a PBS solution supplemented with Tween-20 at 0.1%.

The primary anti-Ku antibody was then recognized by a secondary goat anti-mouse antibody coupled to peroxidase, diluted 1/10,000 in the same buffer as the primary antibody in an incubation of 30 minutes.

The wells were then washed five times with a PBS solution supplemented with Tween-20 at 0.1%.

A luminescent peroxidase substrate (Specichrom, sold by Speci, Ste Foy-les-Lyon, France) is then added and the whole was incubated for 15 minutes at 30° C., with stirring.

The light signal emitted was measured by a Victor (Wallac OY, Turku, Finland).

Figure 3:
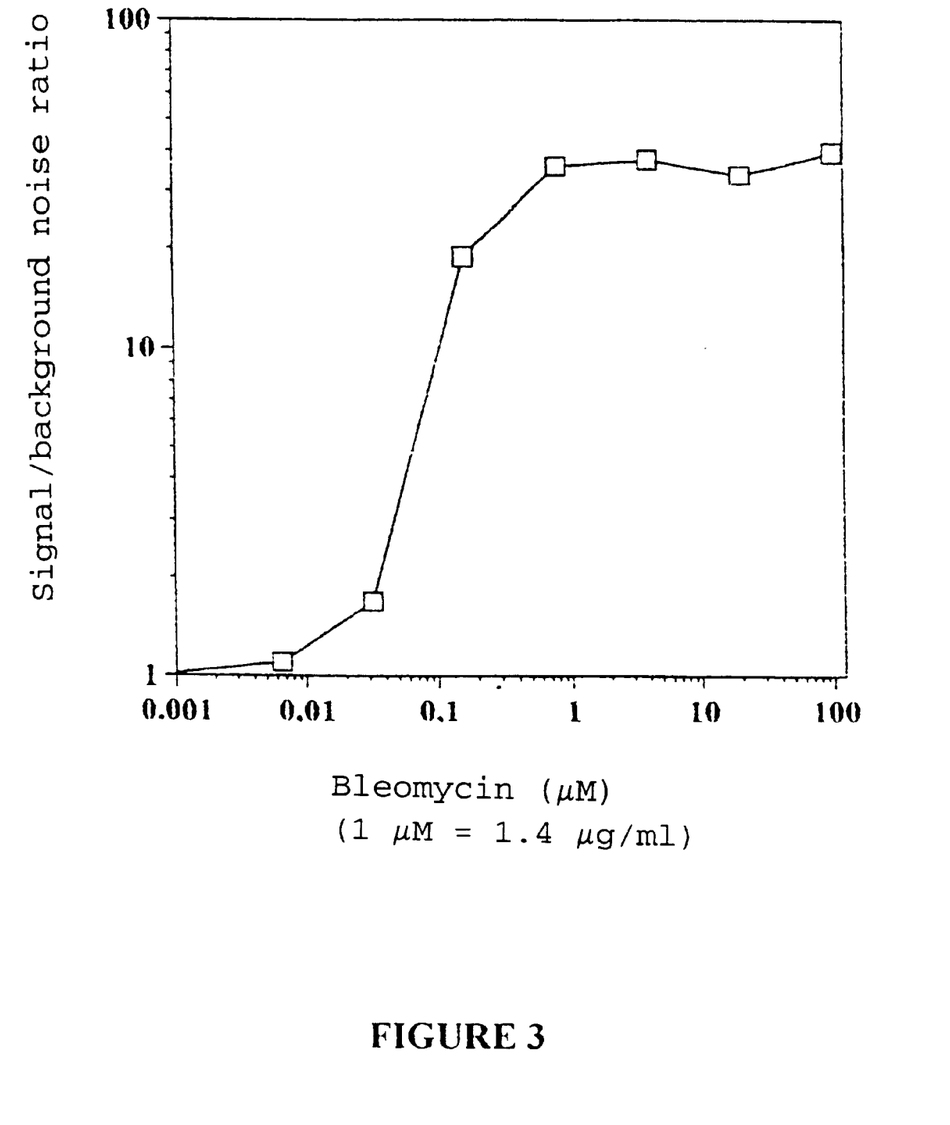
FIG. 3: Recognition of double strand breaks induced by bleomycin by the Ku protein in a cell extract and detection by an anti-Ku monoclonal antibody This graph represents the signal obtained (signal/background noise ratio) as a function of increasing bleomycin concentrations.

The result is expressed as the ratio of the specific signal to the untreated plasmid signal and an example of a result is given in FIG. 3.

There is thus shown, at this stage of the development of the test, a detection threshold of 0.032 µM (32nM) for the double strand breaks generated by bleomycin in the presence of 0.5 µM FeCl$_2$.

Example 3

Detection of DNA Base Mismatches

This type of impairment of the DNA is detected with a protein complex. The recognition of the mismatch is ensured by the hMSH2 protein.

In practice, 37-mer oligonucleotides were synthesized so as to generate a perfect pairing or a mismatch site (the base introducing the mismatch is underlined).

The following sequences (Fishel et al., 1994, Science, 266? 1403–1405) were synthesized:

MIS-C 5' ATGTGAATCAGTATGGTTCCTATCTGCT-GAAGGAAAT 3'(SEQ ID NO:1)

MIS-T 5' ATGTGAATCAGTATGGTTTCTATCTGCT-GAAGGAAAT 3'(SEQ ID NO:2)

MIS-Grev 5' AATTCCTTCAGCAGATAGGAACCAT-ACTGATTCACAT 3'(SEQ ID NO:3)

The oligonucleotides are solubilized at 1 mg:ml in TEIX.

The pairing (hybridization) is carried out in 200 µl, at 400 µg/ml of each oligo, in the presence of 1M NaCl.

The tubes were heated at 100° C. for 10 minutes in a thermocycler and allowed to cool for 3 hours.

The DNA is then precipitated by addition of 2.5 volumes of absolute ethanol, kept overnight at −20° C. and then centrifuged at 14,000 rpm at 4° C. for 40 minutes. After washing the pellets in 70% ethanol and drying, the pellets are taken up in 1.5 ml of TEIX (at a final concentration of 100 µg/ml).

The MIS-C+MIS-Grev hybridization leads to a normally paired double-stranded DNA (C:G) whereas the MIS-C+MIS-T hybridization leads to a double-stranded DNA comprising a mismatch (C:T).

The DNA was adsorbed onto wells coated with polylysine at the rate of 200 ng per well.

After incubating for 30 minutes, the wells were washed twice with a PBS solution supplemented with Tween-20 at 0.1%.

The wells were then saturated with the aid of a solution of BSA at 3% in PBS for 1 hour at 30° C., with stirring.

The wells were then washed once with a PBS solution supplemented with Tween-20 at 0.1%.

The DNA treated was then incubated with a cell extract of the Manley type [Manley et al. (1980) Proc. Natl. Acad. Sci. USA, 77, 3855–3859], modified by Wood [Wood et al. (1988) Cell, 53, 97–106] for 90 minutes at 30° C. in a buffer containing 40 mM Hepes; 5 mM MgCl$_2$; 50 mM KCl; 0–5 mM DTT; 10 mM phosphocreatine; 0.1 mg/ml BSA; 50 µg/ml creatine phosphokinase; 2 mM EGTA, pH 7.6.

The wells were then washed twice with a PBS solution supplemented with Tween-20 at 0.1%.

The attachment of the hMSH2 protein was revealed by incubating an anti-hMSH2 monoclonal antibody diluted to 2 µg/ml in PBS supplemented with 0.1% BSA and Igepal CA-630 (sold by Sigma) for 2 hours at 30° C., with stirring.

The wells were then washed three times with a PBS solution supplemented with Tween-20 at 0.1%.

The primary anti-hMSH2 antibody was then recognized by a secondary goat anti-mouse antibody coupled to peroxidase, diluted 1/10,000 in the same buffer as the primary antibody in an incubation of 30 minutes.

The wells were then washed five times with a PBS solution supplemented with Tween-20 at 0.1%.

A luminescent peroxidase substrate (Specichrom, sold by Speci, Ste Foy-les-Lyon, France) is then added and the whole was incubated for 15 minutes at 30° C., with stirring.

The light signal emitted was measured by a Victor (Wallac OY, Turku, Finland).

The ratio of the specific signal (oligonucleotide carrying a mismatch; T:G) to the signal for the oligonucleotide not carrying a mismatch (C:G) was 5.

EXAMPLE 4

Application to the Detection of Differences in Double Strand Break Repair Capacity in Cells from Patients Carrying a Mutated ATM Gene or Otherwise The lymphoblastoid cells, derived from healthy patients, heterozygous or homozygous for the ATM (Ataxia telangectasia; leading to hypersensitivity to ionizing radiation) gene, in culture were irradiated at doses of 0, 1 and 3 Gy. The doses of 1 and 3 Gy have the effect of generating DNA double strand breaks which will be detected by means of the recognition of the Ku-DNA$^{PK}$ complex as described in Example 2.

The cells are then cultured in a suitable medium for 12 and 24 hours, at which times they are washed and frozen at −80° C.

They are then lysed and the genomic DNA adsorbed onto the wells as in the preceding examples.

After incubating for 30 minutes, the wells were washed twice with a PBS solution supplemented with Tween-20 at 0.1%.

The wells were then saturated with the aid of a solution of BSA at 3% in PBS for 1 hour at 30° C., with stirring.

The wells were then washed once with a PBS solution supplemented with Tween-20 at 0.1%.

The DNA treated was then incubated with a cell extract of the Manley type [Manley et al. (1980) Proc. Natl. Acad. Sci. USA, 77, 3855–3859], modified by Wood [Wood et al. (1988) Cell, 53, 97–106] for 90 minutes at 30° C. in a buffer containing 40 mM Hepes; 5 mM MgCl$_2$; 50 mM KCl; 0.5 mM DTT; 10 mM phosphocreatine; 0.1 mg/ml BSA; 50 µg/ml creatine phosphokinase; 2 mM EGTA, pH 7.6.

The wells were then washed twice with a PBS solution supplemented with Tween-20 at 0.1%.

The attachment of the Ku complex was revealed by incubating an anti-Ku monoclonal antibody diluted to 100 ng/ml in PBS supplemented with 0.1% BSA and Igepal CA-630 (sold by Sigma) for 2 hours at 30° C., with stirring.

The wells were then washed three times with a PBS solution supplemented with Tween-20 at 0.1%.

The primary anti-Ku antibody was then recognized by a secondary goat anti-mouse antibody coupled to peroxidase, diluted 1/10,000 in the same buffer as the primary antibody in an incubation of 30 minutes.

The wells were then washed five times with a PBS solution supplemented with Tween-20 at 0.1%.

A luminescent peroxidase substrate (Specichrom, sold by Speci, Ste Foy-les-Lyon, France) is then added and the whole was incubated for 15 minutes at 30° C., with stirring.

The light signal emitted was measured by a Victor (Wallac OY, Turku, Finland).

Figure 4:
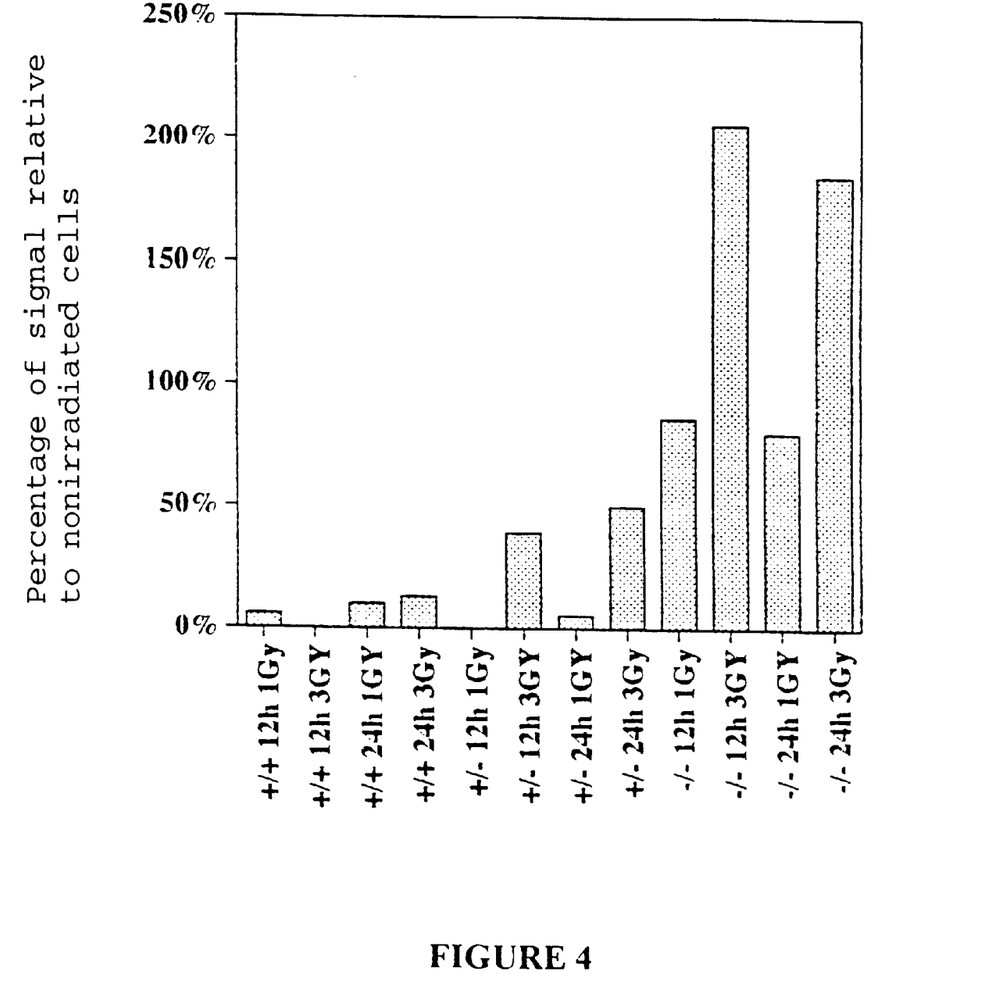
FIG. 4: Measurement of the persistence of double strand breaks radio-induced by the Ku protein in a cell extract and detection by an anti-Ku monoclonal antibody +/+ designates the cells nonmutated for the ATM gene +/− represents the mutated cells heterozygous for the ATM gene −/− designates the mutated cells homozygous for the ATM gene 12 h and 24 h represent the times for post-incubation with irradiation 1Gy and 3Gy (Gray) define the irradiation doses An advantageous embodiment of the present invention is based on the principle of the test called GeneTEX.

The result is expressed as the ratio of the specific signal to the untreated plasmid signal and an example of a result is given in FIG. 4.

It is thus shown that the test is in particular applicable to the measurement of the radiosensitivity of cells derived from patients. Depending on the kinetics of repair of the breaks induced by ionizing radiation, it is possible to discriminate between the homozygous ATM patients, the heterozygous ATM patients and the patients carrying no mutation in this gene.

At the dose of 3 Gy, the DNA breaks are less well repaired in the patients heterozygous for the ATM gene as shown by the percentage of breaks which persist.

According to the same principle, it is possible to detect any sensitivity to ionizing radiation, whether it is due to a deficiency in ATM or in another gene.

EXAMPLE 5

Detection of Lesions in DNA Recognized by the NER System by an Anti-XPA Antibody and the DELFA® Technique The DNA (plasmid pUC18) was prelesioned with UVC or with cisplatin as described in Example 1.

The DNA, prelesioned with UVC or with cisplatin, was adsorbed onto wells coated with polylysine at the rate of 50 ng per well. As a control, DNAs carrying oxidative lesions (lesions generated by illumination in the presence of methylene blue), repaired by the BER system were used.

After incubating for 30 minutes, the wells were washed twice with a PBS solution supplemented with Tween-20 at 0.1%.

The wells were then washed twice with a TBS (Tris buffer saline) solution supplemented with Tween-20 at 0.1%.

The wells were then saturated with the aid of a solution of BSA at 3% in TBS for 1 hour at 30° C., with stirring.

The wells were then washed once with a TBS solution supplemented with Tween-20 at 0.1%.

The DNA treated was then incubated with a cell extract of the Manley type [Manley et al. (1980) Proc. Natl. Acad. Sci. USA, 77, 3855–38591], modified by Wood [Wood et al. (1988) Cell, 53, 97–106] for 90 minutes at 30° C. in a buffer containing 40 mM Hepes; 5 mM $MgCl_2$; 50 mM KCl; 0.5 mM DTT; 10 mM phosphocreatine; 0.1 mg/ml BSA; 50 µg/ml creatine phosphokinase; 2 mM EGTA, pH 7.6.

The wells were then washed twice with a TBS solution supplemented with Tween-20 at 0.1%.

The attachment of the XPA protein was revealed by incubating an anti-XPA monoclonal antibody diluted to 500 ng/ml in TBS supplemented with 0.1% BSA and Igepal CA-630 (sold by Sigma) for 2 hours at 30° C., with stirring. This antibody was labeled beforehand with an average of 10 Europium ($Eu^{3+}$) chelates according to the Wallac protocol.

The wells were then washed eight times with a TBS solution supplemented with Tween-20 at 0.1%.

The revealing solution ("Enhancement Solution", Wallac) is then added (50 µl/well) and the plate vigorously stirred for 5 minutes. The fluorescence ("Time Resolved Fluorescence") emitted was measured by a Victor (Wallac OY, Turku, Finland) according to the DELFIA protocol suitable for Europium chelates.

The result is expressed as the ratio of specific signal to the untreated plasmid signal and is similar to the result shown in FIG. 1.

There was thus shown, at this stage of development of this test, a detection threshold also of 30 $J/m^2$ for the UVC lesions.

The delfia technology has thus been successfully adapted to the method according to the invention.

---

What is claimed is:

1. A method for detecting an impairment of DNA sequence, comprising:
   contacting a sample DNA with a composition comprising at least one recognition protein selected from the group consisting of proteins belonging to the nucleotide excision repair (NER) system, proteins belonging to the base excision repair (BER) system, and proteins belonging to the system for detecting DNA breaks;
   labeling said at least one recognition protein; and
   detecting a complex formed between the at least one labeled recognition protein and DNA;
      wherein detecting said complex detects impairment of the DNA sequence.

2. The method according to claim 1, further comprising:
   contacting a control DNA with a composition comprising at least one recognition protein selected from the group consisting of proteins belonging to the nucleotide excision repair (NER) system, proteins belonging to the base excision repair (BER) system, and proteins belonging to the system for detecting DNA breaks;
   labeling said at least one recognition protein; and
   detecting a complex formed between the at least one labeled recognition protein and DNA;
      wherein detecting said complex detects impairment of the DNA sequence; and
      comparing impairment of DNA sequence in sample DNA to impairment of DNA sequence in control DNA.

3. The method according to claim 1, wherein the composition comprising at least one recognition protein comprises a cell extract.

4. The method according to claim 1, wherein the recognition protein is a protein belonging to the nucleotide excision repair (NER) system.

5. The method according to claim 1, wherein the recognition protein is a protein belonging to the base excision repair (BER) system.

6. The method according to claim 1, wherein the recognition protein is a protein belonging to the system for detecting DNA breaks.

7. The method according to claim 1, wherein said complex is detected with a labeled ligand.

8. The method according to claim 1, wherein said complex is detected with a labeled antibody.

9. The method according to claim 1, wherein the sample DNA is at least partially purified.

10. The method according to claim 1, wherein the sample DNA is a total cell extract.

11. The method according to claim 1, wherein the sample DNA is attached to a solid support.

12. The method according to claim 1, wherein the method is performed in a liquid system.

13. The method according to claim 12, wherein the method is performed in a time-resolved amplified cryptate emissions system.

14. The method of claim 1, wherein the composition comprising at least one recognition protein further comprises at least two different compounds selected from the group consisting of compounds for detecting binding of said DNA to a protein belonging to the nucleotide excision repair (NER) system, compounds for detecting binding of said DNA to a protein belonging to the base excision repair (BER) system, and compounds for detecting binding of said DNA to proteins belonging to the system for detecting DNA breaks.

15. The method of claim 14, further comprising detecting said at least two compounds.

16. The method of claim 2, further comprising:
   obtaining said sample DNA from a first environment; and
   obtaining said control DNA from a second environment;
      wherein impairment of DNA sequence in said sample DNA greater than the impairment of DNA sequence in control DNA identifies a greater incidence of genotoxic properties in said first environment relative to said second environment.

* * * * *

SEQUENCE LISTING

```
<160> NUMBER OF SEQ ID NOS:  3

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide for detecting mismatch.
<223> OTHER INFORMATION: MIS-C

<400> SEQUENCE: 1
atgtgaatca gtatggttcc tatctgctga aggaaat                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide for detecting mismatch.
<223> OTHER INFORMATION: MIS-T

<400> SEQUENCE: 2
atgtgaatca gtatggtttc tatctgctga aggaaat                              37

<210> SEQ ID NO 3
<211> LENGTH: 37
<212> TYPE: DNA
<213> ORGANISM: Artificial Sequence
<220> FEATURE:
```

```
<223> OTHER INFORMATION: Description of Artificial Sequence:
      Oligonucleotide for detecting mismatch.
<223> OTHER INFORMATION: MIS-Grev

<400> SEQUENCE: 3
aattccttca gcagatagga accatactga ttcacat                          37
```